United States Patent [19]

Koehler et al.

[11] Patent Number: 4,864,030

[45] Date of Patent: Sep. 5, 1989

[54] PREPARATION OF 1-ALKYLIMIDAZOLES

[75] Inventors: Hermann Koehler, Beindersheim; Toni Dockner, Meckenheim; Helmut Karn, Ludwigshafen, all of Fed. Rep. of Germany

[73] Assignee: BASF Aktiengesellschaft, Ludwigshafen, Fed. Rep. of Germany

[21] Appl. No.: 238,121

[22] Filed: Aug. 30, 1988

[30] Foreign Application Priority Data

Sep. 5, 1987 [DE] Fed. Rep. of Germany ....... 3729852

[51] Int. Cl.$^4$ .......................................... C07D 233/90
[52] U.S. Cl. .................................... 548/343
[58] Field of Search ........................ 548/343

[56] References Cited

U.S. PATENT DOCUMENTS 4,672,128 6/1987 Kempe et al. ................... 548/343
4,704,459 11/1987 Tudo et al. ..................... 544/362 X

OTHER PUBLICATIONS

R. Jones *J. Am. Chem. Soc.*, vol. 71, pp. 644–647 (1949).
K. Takahashi, et al., *Bull. Chem. Soc. Japan*, 53, pp. 557–558 (1980).
*J. Chem. Soc.* pp. 21–32 (1928), W. Hubball et al.

*Primary Examiner*—Richard A. Schwartz
*Attorney, Agent, or Firm*—Oblon, Spivak, McClelland, Maier & Neustadt

[57] ABSTRACT

Process for the preparation of 1-alkylimidazoles of the general formula (I)

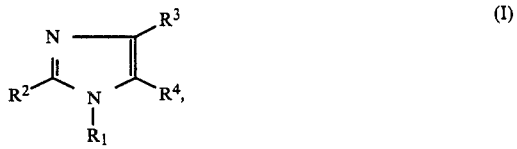

where $R^1$ is alkyl, $R^2$ and $R^3$ are hydrogen, alkyl, aryl, arylalkyl, or alkylaryl, $R^4$ is carboxy, alkoxycarbonyl $R^5OCC-$, carbamoyl, or cyano, and $R^5$ is an alkyl of from 1 to 8 carbon atoms—by the reaction of imidazoles of the general formula (II)

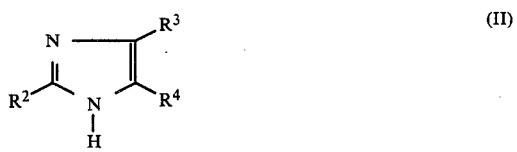

with dialkyl sulfates of the general formula (III)

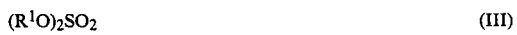

$(R^1O)_2SO_2$      (III)

at elevated temperatures in the presence of a carboxylic acid or anhydride or of both acid and anhydride.

4 Claims, No Drawings

PREPARATION OF 1-ALKYLIMIDAZOLES

The present invention relates to a novel, improved process for the preparation of 1-alkylimidazoles by treating imidazoles with dialkyl sulfates at elevated temperatures in the presence of a carboxylic acid or anhydride or of both acid and anhydride.

It is known from *J. Am. Chem. Soc.*, 71, 644–7 (1949) that methyl 1-methylimidazole-5-carboxylate can be obtained with an overall yield of 35% from the methyl ester of N-methylglycine hydrochloride in a three-stage reaction.

Also known is the preparation of 1-methylimidazole-5-carboxylic acid by selective decarboxylation of 1-methylimidazole-4,5-dicarboxylic acid, described in *Bull. Chem. Soc. Japan*, 53, 557–8 (1980).

The formation of methyl 1-methylimidazole-5-carboxylate in 37% yield by the treatment of methyl imidazole-4(5)-carboxylate with dimethyl sulfate in the absence of solvent is known from *J. Chem. Soc.*, 21–3 (1928).

The aim of the present invention was to find a new or improved preparative route to 1-alkylimidazoles. We have found that this aim is achieved by a novel, improved process for the preparation of 1-alkylimidazoles of the general formula (I)

where $R^1$ is alkyl, $R^2$ and $R^3$ are hydrogen, alkyl, aryl, arylalkyl, or alkylaryl, $R^4$ is carboxy, alkoxycarbonyl $R^5OOC-$, carbamoyl, or cyano, and $R^5$ is an alkyl of from 1 to 8 carbon atoms—by the reaction of imidazoles of the general formula (II)

with dialkyl sulfates of the general formula (III)

at elevated temperatures in the presence of a carboxylic acid or anhydride or of both acid and anhydride.

The 1-alkylimidazoles (I) can be obtained by the following method.

The reaction between an imidazole (II) and a dialkyl sulfate takes place at elevated temperatures in the presence of a carboxylic acid or anhydride or both in accordance with the scheme

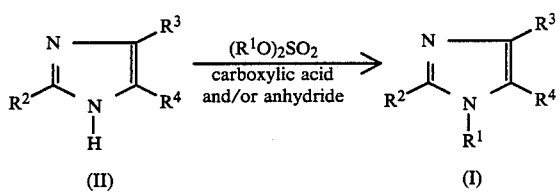

Preferably the reaction is carried out at from 40° C. to 220° C., particularly from 80° C. to 150° C., under atmospheric pressure, but it can be carried out under elevated pressures up to 10 bar and reduced pressures down to 0.1 bar.

The process can be performed continuously or batchwise.

The imidazole-4(5)-carboxylic acids are mostly known and can be prepared by the process described in DE-A 34 27 136. The corresponding esters of imidazole-4(5)-carboxylic acids and imidazole-4(5)-carboxamides can be prepared from the imidazole-4(5)-carboxylic acids by methods that are generally known. The imidazole-4(5)-carbonitriles can be obtained by treating the imidazole-4(5)-carboxamides with substances with an affinity for water, such as phosphorus pentachloride or phosphoryl trichloride.

The mole ratio of dialkyl sulfate to imidazole (II) is from 0.4:1 to 10:1, preferably from 0.5:1 to 3:1.

Suitable carboxylic acids are unbranched and branched aliphatic carboxylic acids of from 1 to 8 carbon atoms, preferably unbranched or branched acids of from 1 to 6 carbon atoms, such as formic, acetic, propionic, butyric, isobutyric, valeric, isovaleric, pivalic, and caproic acids; formic, acetic, and propionic acids are particularly preferred.

Suitable carboxylic anhydrides are unbranched and branched aliphatic carboxylic anhydrides of from 4 to 16 carbon atoms, preferably unbranched and branched aliphatic carboxylic anhydrides of from 4 to 12 carbon atoms, such as acetic, propionic, butyric, isobutyric, valeric, isovaleric, pivalic, and caproic anhydrides and mixed anhydrides; acetic anhydride is particularly preferred.

Mixtures of carboxylic acids and anhydrides or mixed anhydrides (or both) are also suitable.

Both carboxylic acids and anhydrides are suitable, but the anhydrides are given special preference.

The quantities of carboxylic acids and/or anhydrides employed are such that stirrable reaction mixtures are formed. Preferably the volume of acid and/or anhydride is from 40 ml to 2000 ml—in particular from 100 ml to 500 ml—per mole of imidazole (II). Larger volumes of carboxylic acid and/or anhydride are generally unnecessary, but can be used.

Treatment of the mixtures subsequent to the reactions is conventional, for instance addition of water, separation of the phases, and column chromatography. Some of the products of general formula (I) occur as colorless or slightly brownish viscous oils; these can be purified by prolonged heating at moderate temperatures under reduced pressure ('incipient distillation'), which frees them from the last volatile components. Those products of general formula (I) that are obtained as crystals can be purified by recrystallization.

The substituents $R^1, R^2, \ldots R^5$ in the general formulae (I), (II), and (III) are as follows.

$R^1$: Normal or branched alkyl, preferably normal or branched alkyl of from 1 to 20 carbon atoms; especially preferred are normal and branched alkyls of from 1 to 12 carbon atoms, such as methyl, ethyl, propyl, isopropyl, butyl, isobutyl, sec-butyl, tert-butyl, pentyl, isopentyl, sec-pentyl, tert-pentyl, neopentyl, 1,2-dimethylpropyl, hexyl, isohexyl, sec-hexyl, heptyl, isoheptyl, octyl, isooctyl, nonyl, isononyl, decyl, isodecyl, undecyl, isoundecyl, dodecyl, and isododecyl.

$R^2$ and $R^3$: Independently either hydrogen;

alkyl, normal or branched, preferably normal or branched alkyl of from 1 to 20 carbon atoms; especially preferred are normal and branched alkyls of from 1 to 12 carbon atoms, such as methyl, ethyl, propyl, isopropyl, butyl, isobutyl, sec-butyl, tert-butyl, pentyl, isopentyl, sec-pentyl, tert-pentyl, neopentyl, 1,2-dimethylpropyl, hexyl, isohexyl, sec-hexyl, heptyl, isoheptyl, octyl, isooctyl, nonyl, isononyl, decyl, isodecyl, undecyl, isoundecyl, dodecyl, and isododecyl;

aryl, preferably phenyl, 1-naphthyl, 2-naphthyl, 1-anthryl, 2-anthryl, or 9-anthryl; phenyl is especially preferred;.

arylalkyl, unbranched or branched; preferred are unbranched and branched phenylalkyls of from 7 to 10 carbon atoms, such as benzyl, 1-phenylethyl, phenethyl, 1-phenylpropyl, 2-phenylpropyl, and 3-phenylpropyl;

or alkylaryl, unbranched or branched, preferably unbranched or branched alkylaryl of from 7 to 20 carbon atoms; especially preferred are unbranched or branched alkylphenyls of from 7 to 10 carbon atoms, such as 2-methylphenyl, 3-methylphenyl, 4-methylphenyl, 2-ethylphenyl, 3-ethylphenyl, 4-ethylphenyl, 2-propylphenyl, 3-propylphenyl, 4-propylphenyl, 2-isopropylphenyl, 3-isopropylphenyl, 4-isopropylphenyl, 2-butylphenyl, 3-butylphenyl, 4-butylphenyl, 2-isobutylphenyl, 3-isobutylphenyl, 4-isobutylphenyl, 2-sec-butylphenyl, 3-sec-butylphenyl, 4-sec-butylphenyl, 2-tert-butylphenyl, 3-tert-butylphenyl, 4-tert-butylphenyl, 2,4-dimethylphenyl, 3,4-dimethylphenyl, 2,6-dimethylphenyl, 3,4-diethylphenyl, 3,4,5-trimethylphenyl, 2,4,6-trimethylphenyl, and 2-ethyl-4-methylphenyl.

$R^4$: Carboxy, $R^5$-oxycarbonyl, carbamoyl, or cyano.

$R^5$: Normal or branched alkyl of from 1 to 8 carbon atoms; preferred are normal or branched alkyls of from 1 to 4 carbon atoms, such as methyl, ethyl, propyl, isopropyl, butyl, isobutyl, sec-butyl, and tert-butyl.

If the group $R^4$ in the compounds of general formulae (I) and (II) is carboxy, it is better to isolate the compounds (I) as the $R^5$-esters rather than the free acids, unless the free acids are particularly required.

The compounds of general formula (I) are intermediates for the synthesis of active substances.

The following examples illustrate the invention.

EXAMPLE 1

Preparation of 1-methylimidazole-5-carboxylic acid

Over a period of 1 h 252 g (2 mol) of dimethyl sulfate was added dropwise to a solution of 112 g (1 mol) of imidazole-4(5)-carboxylic acid in 200 ml of acetic anhydride at a temperature of 110° C. The mixture was heated under reflux for a further 3 h, then the volatile components were removed by distillation.

To characterize the 1-methylimidazole-5-carboxylic acid it was converted into its methyl ester, as follows.

The residue obtained as described above was refluxed with 300 ml of methanol and 150 ml of concentrated sulfuric acid for 2 h, then the excess methanol was distilled off. The residue was diluted with 250 ml of water, neutralized with concentrated ammonia solution, and extracted with methylene chloride. After the extract had been dried and freed from solvent in vacuo, 105.1 g of methyl 1-methylimidazole-5-carboxylate, m.p. 44°–46° C., was obtained, an overall yield of 75%.

$^1$H-NMR (CDCl$_3$): 3.86 ppm (s, 3H), 3.91 ppm (s, 3H), 7.58 ppm (s, 1H), 7.72 ppm (s, 1H).

$^{13}$C-NMR (CDCl$_3$): 34.0 ppm, 51.4 ppm, 123.1 ppm, 137.6 ppm, 142.6 ppm, 160.8 ppm (all signals s).

EXAMPLE 2

Preparation of 1-ethylimidazole-5-carboxylic acid

Over a period of 1 h 308 g (2 mol) of diethyl sulfate was added dropwise to a solution of 112 g (1 mol) of imidazole-4(5)-carboxylic acid in 200 ml of acetic anhydride at a temperature of 110° C. The mixture was heated under reflux for a further 3 h, then the volatile components were removed by distillation.

To characterize the 1-ethylimidazole-5-carboxylic acid its methyl ester was formed and then converted into the hydrochloride of the acid, as follows.

The residue obtained as described above was refluxed with 300 ml of methanol and 150 ml of concentrated sulfuric acid for 2 h, then the excess methanol was distilled off. The residue was diluted with 250 ml of water, neutralized with concentrated ammonia solution, and extracted with methylene chloride. After the extract had been dried and freed from solvent in vacuo, methyl 1-ethylimidazole-5-carboxylate was obtained. This was heated with 6N hydrochloric acid for 4 h, then the mixture was evaporated down. Recrystallization of the product from methanol gave 95.3 g of the hydrochloride of 1-ethylimidazole-5-carboxylic acid, m.p. 238°–239° C. (decomp.), an overall yield of 54%.

For C$_6$H$_9$N$_2$O$_2$Cl (M=176.6 g/mol)—Calc.: C 40.8; H 5.1; N 15.9; Cl 20.1%. Found: C 40.8; H 5.1; N 15.7; Cl 20.2%.

$^1$H-NMR (DMSO-d$_6$): 1.45 ppm (t, 3H), 4.53 ppm (q, 2H), 8.35 ppm (s, 1H), 9.55 ppm (s, 1H).

$^{13}$C-NMR (DMSO-d$_6$): 15.5 ppm, 43.7 ppm, 124.0 ppm, 126.5 ppm, 138.6 ppm, 158.9 ppm (all signals s).

EXAMPLE 3

Preparation of 1,2-dimethylimidazole-5-carboxylic acid

In the manner described in Example 1 126 g (1 mol) of 2-methylimidazole-4(5)-carboxylic acid was treated with dimethyl sulfate and the product was converted into its methyl ester for characterization. This gave 103.3 g of methyl 1,2-dimethylimidazole-5-carboxylate, m.p. 38°–40° C., an overall yield of 67%.

For C$_8$H$_{10}$N$_2$O$_2$ (M=154.2 g/mol)—Calc.: C 54.5; H 6.5; N 18.2%. Found: C 54.2; H 6.6; N 18.0%.

$^1$H-NMR (CDCl$_3$): 2.42 ppm (s, 3H), 3.83 ppm (s, 6H), 7.62 ppm (s, 1H).

$^{13}$C-NMR (CDCl$_3$): 13.4 ppm, 32.1 ppm, 51.2 ppm, 122.9 ppm, 136.2 ppm, 150.4 ppm, 160.9 ppm (all signals s).

EXAMPLE 4

Preparation of methyl 1-methylimidazole-5-carboxylate

Over a period of 1 h 252 g (2 mol) of dimethyl sulfate was added dropwise to a solution of 126 g (1 mol) of methyl imidazole-4(5)-carboxylate in 250 ml of acetic anhydride at a temperature of 110° C. The mixture was heated under reflux for a further 3 h, then the volatile components were removed by distillation.

The residue was diluted with 250 ml of water, neutralized with concentrated ammonia solution, and extracted with methylene chloride. After the extract had been dried and freed from solvent in vacuo, 115.0 g of methyl 1-methylimidazole-5-carboxylate, m.p. 44°–46° C., was obtained, an overall yield of 82%.

We claim:

1. A process for preparation of a 1-alkylimidazole of the formula (I)

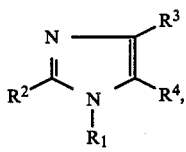
(I)

wherein $R^1$ is alkyl, $R^2$ and $R^3$ are hydrogen, alkyl, aryl, arylalkyl, or alkylaryl, $R^4$ is carboxy, alkoxycarbonyl $R^5OOC-$, carbamoyl, or cyano, and $R^5$ is an alkyl of from 1 to 8 carbon atoms by the reaction of an imidazole of the formula (II)

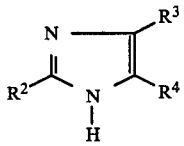
(II)

with a dialkyl sulfate of the formula (III)

(III)

at elevated temperatures in the presence of a carboxylic acid or anhydride or of both acid and anhydride.

2. A process as claimed in claim 1 wherein the reaction is carried out in an aliphatic carboxylic acid of from 1 to 8 carbon atoms, or an aliphatic carboxylic anhydride of from 4 to 16 carbon atoms, or a mixture of both.

3. A process as claimed in claim 1 wherein the reaction is carried out in an aliphatic carboxylic anhydride of from 4 to 12 carbon atoms.

4. A process as claimed in claim 1 wherein the reaction is carried out in the presence of from 40 ml to 2000 ml of a carboxylic acid or anhydride or of both acid and anhydride per mole of the imidazole (II).

* * * * *